US006458770B1

(12) United States Patent
Van Hoogevest

(10) Patent No.: US 6,458,770 B1
(45) Date of Patent: Oct. 1, 2002

(54) PARENTERAL FORMULATIONS COMPRISING CARBAMAZEPINE OR ITS DERIVATIVES

(75) Inventor: Peter Van Hoogevest, Bubendorf (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/037,090

(22) Filed: Nov. 9, 2001

Related U.S. Application Data

(63) Continuation of application No. 09/509,973, filed as application No. PCT/EP98/06382 on Oct. 7, 1998, now Pat. No. 6,316,417.

(30) Foreign Application Priority Data

Oct. 9, 1997 (GB) ............................................. 9721497

(51) Int. Cl.$^7$ ................................................ A61K 31/70
(52) U.S. Cl. ......................................... 514/25; 514/217
(58) Field of Search .................................. 514/25, 217

(56) References Cited

U.S. PATENT DOCUMENTS

| 5,231,089 A | * | 7/1993 | Bodor ........................... 514/58 |
| 5,284,662 A | * | 2/1994 | Koparkar et al. ............ 424/473 |
| 5,466,683 A | * | 11/1995 | Sterling et al. ............... 514/80 |
| 5,624,945 A | | 4/1997 | Bousseau et al. ............ 514/367 |
| 5,629,312 A | | 5/1997 | Bousseau et al. ............ 514/242 |
| 5,695,782 A | * | 12/1997 | Bourquin ..................... 424/472 |

FOREIGN PATENT DOCUMENTS

| EP | 0435825 A | * | 7/1991 |
| EP | 0 435 826 A | | 7/1991 |
| IE | 904685 | | 7/1991 |
| WO | 94 20110 A | * | 9/1994 |

OTHER PUBLICATIONS

Farago, "Trigeminal Neuralgi: Its Treatment With Two New Carbamazepine Analogues," European Neurology, vol. 26(2), pp. 73–83 (1987) Switzerland XP002089864.

Reynolds, James E.F., "Martindale The Extra Pharmacopoeia," The Pharmacuetical Press, London Great Britain XP002089865, pp. 295–298; esp. p. 298, left column, l. 19–21 (1993).

"Fass 1996 Läkemedel I Sverige Förteckning över humanläkemedel," Linfo Läkemedelsinformation AB, Sweden XP002089866, p. 992: Tegretol mixtur (1996).

* cited by examiner

Primary Examiner—James H Reamer
(74) Attorney, Agent, or Firm—John D. Thallemer

(57) ABSTRACT

The invention is concerned with a parenteral formulation comprising a 5H-dibenz(b,f)azepine-5-carboxamide and an aqueous-based solvent. The parenteral formulation is useful in the treatment of seizures resulting from, e.g. epileptic attack.

2 Claims, No Drawings

PARENTERAL FORMULATIONS COMPRISING CARBAMAZEPINE OR ITS DERIVATIVES

This application is a continuation of application Ser. No. 09/509,973 filed May 2, 2000, now U.S. Pat No. 6,318,417, which is a 371 of PCT/EP98/06382, filed Oct. 7, 1998, which in its entirety is herein incorporated by reference.

This invention relates to parenteral formulations of 5H-dibenz(b,f)azepine-5-carboxamides.

5H-dibenz(b,f)azepine-5-carboxamides are known anti-convulsants useful in the treatment of seizures resulting from, for example an epileptic attack.

Oral forms of 5H-dibenz(b,f)azepine-5-carboxamides are known and are suitable for repeat administration over a prolonged period of treatment to ensure a uniform concentration of active agent in the blood. However, in emergency situations oral administration to an epileptic patient may not be possible and in any case may not provide the necessary immediate response.

Accordingly, there is a need to develop parenteral formulations, in particular which are suitable for use intravenously, of an anticonvulsant based on 5H-dibenz(b,f)azepine-5-carboxamides.

It has now been found that 5H-dibenz(b,f)azepine-5-carboxamides may be formulated as a parenteral formulation in water optionally with an organic co-solvent.

The invention provides in one of its aspects a parenteral formulation comprising as active agent a 5H-dibenz(b,f)azepine-5-carboxamide and a solvent consisting of water and optionally an organic co-solvent and no other solubilising aids.

By solubilising aids is meant any compounds that assist in solubilising drug molecules by accommodating a drug molecule in a cavity formed in the solubilising aid to form inclusion complexes. Said solubilising aids are in particular the cyclodextrins, more particularly beta-cyclodextrin.

The parenteral formulation may be suitable for administering intravenously. The immediate response of this form of administration is highly desirable in emergency situations. Furthermore, as no absorption process is involved, the dose or blood concentration of active agent may be obtained with greater accuracy and speed.

The active agents and the syntheses for preparing same are Known in the art. The active agents may be substituted or unsubstituted at the 10- or 11-position. The 10-or 11-position may be substituted with mono- or divalent substituents selected from oxa, halogen or hydroxy groups, preferably oxa- or hydroxy groups.

When there is an oxa-or a hydroxy group at the 10-position, the 11-position is preferably unsubstituted and vice versa.

Preferred compounds are selected from carbamazepine (Tegretol®), 10-oxacarbazepine (Trileptal ®) and 10-hydroxy-10,11-tetrahydrocarbamazepine (hereinafter referred to as COMPOUND A). COMPOUND A has a chiral centre and may be used as its racemic mixture.

We have now found that COMPOUND A, which has not previously been commercially available may be made up to a commercially acceptable, well tolerated and stable formulation, e.g. from 3 months up to 2 or even 3 years, for intravenous administration.

Preferred active agents, e.g. COMPOUND A may have a solubility in water of up to 4.5 mg/ml, preferably 3.2 to 4.2 mg/ml, more preferably 2.5 at 25° C. and preferably at a pH of 4.0 to 7.0. Within these ranges of solubility, the active agents are advantageously formulated without the need for an organic co-solvent or any other solubilisingaid.

In parenteral formulations suitable for adminstration intravenously, the solvent for the active agent is either water or is aqueous-based. By "aqueous based" is meant a solution consisting of water and a water-miscible organic solvent or solvents. When an organic co-solvent is employed it is preferred that the it is used in amounts of up to 10% by weight, e.g. 0.5 to 10, more particularly 1 to 100% by weight. Suitable solvents are those water-miscible solvents commonly used in the art, for example propyleneglycol, polyethyleneglycol 300, polyethyleneglycol 400 and ethanol. Preferably, organic co-solvents are only used in cases where the active agent is not sufficiently soluble in water for a therapeutically effective amount to be provided in a single dosage form. Preferably the solvent consists solely of water.

As an alternative or in addition to the use of an organic co-solvent it may be useful to employ a solubilisingaid, e.g. cyclodextrins. Cyclodextrins may be useful solubilising aids when the active agent is selected from 10-oxacarbazepine (Trileptal®) and COMPOUND A.

The invention provides in another of its aspects a parenteral formulation, e.g. an i.v. formulation comprising a 5H-dibenz(b,f)azepine-5-carboxamide, e.g. COMPOUND A and a solvent consisting of water.

Preferably the parenteral formulations suitable for intravenous administration are formulated to have the same osmotic pressure as body fluid. Accordingly, a parenteral formulation according to the invention comprises an isotonic agent which has the effect of rendering the osmotic pressure of the formulation the same as that of body fluid.

Accordingly, in another aspect of the invention there is provided a parenteral formulation comprising as active agent a 5H-dibenz(b,f)azepine-5-carboxamide, e.g. COMPOUND A and a solvent consisting entirely of water, or water and an organic co-solvent, and an isotonic agent.

The isotonic agent may be selected from any of those commonly used in the art, e.g. mannitol, sodium chloride, dextran and glucose. As isotonic agents there can be mentioned in particular sodium chloride and glucose.

The isotonic agents may be used in quantities which impart to the parenteral formulation the same osmotic pressure as body fluid. The precise amount necessary to achieve the desired effect may depend on factors such as the concentration of active agent in the parenteral formulation, and is a matter of routine experimentation which the skilled person may determine without exercising any inventive thought and using only common general knowledge.

Selection of the isotonic agent is preferably made having regard to the properties, e.g. stability of the active agent. It has been found that certain isotonic agents, for example sodium chloride may promote the formation of oxidative degradation products of the active agents. This may be particularly problematic when the parenteral formulation is entirely water-based and the degradation product or products of the active agent, e.g. COMPOUND A is insoluble in water.

In order to reduce the likelihood of forming oxidative degradation products it is preferred that, particularly in the case of entirely water-based solutions, the parenteral formulation should be scrupulously purged of air when being packaged. Nevertheless, even if care is taken to purge a filled container of air, Harge Volume parenteral formulations, e.g. larger than 100 ml, more particularly about 250 ml, of an active agent, e.g. COMPOUND A comprising sodium chloride as the isotonic agent, oxidative degradation products may be detected after only relatively short storage periods. Surprisingly, we have found that, in the case of Low Volume parenteral formulations, e.g. about 100 ml or less of active agent, e.g. COMPOUND A, by carefully purging a filled container with nitrogen or other inert gas the formation of oxidative degradation products may be avoided. When the formulations are carefully purged of oxygen, the dissolved oxygen content may be less than 2 mg/ml, e.g. 1 mg/ml or lower.

We have also surprisingly found that even for Harge Volume parenteral formulations of an active agent, e.g. COMPOUND A, by judiciously selecting the type and quantity of isotonic agent the formation of oxidative degradation products may be avoided. This may be the case irrespective of whether the precaution is taken of purging the system of air. Preferably, the isotonic agent is glucose. The use of glucose is particularly advantageous when the injectable solution is entirely water-based and the active agent employed, e.g. COMPOUND A may oxidatively degrade to form a highly water insoluble compound which may even be coloured.

The amount of glucose used will depend upon the concentration of the active agent employed. In preferred formulations glucose may be used in amounts up to 5% by weight, e.g., 0.5 to 5% by weight, based on the weight of the parenteral formulation, more preferably 4.75% by weight.

In a preferred embodiment of the invention there is provided a parenteral formulation comprising an entirely water-based solution of COMPOUND A and glucose.

In the preferred parenteral formulation COMPOUND A is present in a concentration of 2 to 4.5, more preferably 2 to 3.5, e.g. 2.5 mg/ml. Glucose is preferably present in an amount up to 5% by weight e.g., 0.5 to 5% by weight based on the weight of the parenteral formulation, more preferably 4.75%.

Parenteral formulations according to the invention may contain other excipients commonly employed in parenteral formulations for administration intravenously in order to provide the required stability and therapeutic efficacy. Excipients may include antioxidants and acidifying agents and any other excipients commonly used in the preparation of parenteral formulations for intravenous administration.

Antioxidants may be employed to protect the active agent from oxidative degradation particularly under the accelerated conditions of thermal sterilisation. Antioxidants may be selected from any of those compounds known in the art. Similarly, the amount of antioxidant employed can be determined using only routine experimentation. As an alternative to the use of antioxidant compounds, the antioxidant effect can be achieved by displacing oxygen (air) from contact with the solution of active agent. This is usually carried out by purging with, e.g. nitrogen, a container holding the solution.

In another aspect of the invention there is provided a process of preparing an parenteral formulation as hereinabove defined.

The process may be carried out in a conventional manner used in the art of manufacturing parenteral formulations, e.g. i.v. formulations.

The process of preparing a parenteral formulation may be carried out in an inert, e.g. stainless steel reactor vessel optionally under an inert atmosphere, e.g. nitrogen. The process comprises the step of adding an isotonic agent, e.g. glucose, optionally in its monohydrate form, to a water or aqueous-based solution of the active agent, e.g. COMPOUND A and optionally other excipients.

Preferably the reaction vessel is charged with water or with water and a water-miscible organic solvent and heated to a temperature of about 80° C. The active agent, e.g. COMPOUND A may be added to the solvent at elevated temperature with stirring.

The isotonic agent may be thereafter added to the solution of active agent. If glucose is used as the isotonic agent-it is advantageously used in the form of its monohydrate to aid solubility. When glucose is used, it may be added to a cooled solution of the active agent, e.g. COMPOUND A in order to avoid any degradation of the glucose. The resultant formulation may then be diluted with water or the aqueous-based solvent to make it up to the final volume for injection.

The resultant parenteral formulation is preferably maintained under an inert atmosphere and is transferred to containers, e.g. by a cannular system also under the inert atmosphere. The process for filling containers is discussed hereinbelow.

Solvents other than water, when required, and other reagents may be chosen from medical grade reagents and solvents well known in the art.

Parenteral formulations according to the invention are packaged in containers. Containers may be chosen which are made of material which is non-reactive or substantially non-reactive with the parenteral formulation.

Glass containers may be used although it is preferred to use plastic containers, e.g. plastic infusion bags.

The glass containers may be made of, e.g. soda-lime and borosilicate. Soda-lime glass is referred to USP Type II, whereas the borosilicate glass is referred to as USP Type I. Preferred glass containers are those manufactured by Pharma Hameln FRG.

Plastic containers and in particular plastics infusion bags are preferred over glass containers as they are relatively light weight and non-breakable and thus more easily stored. This is particularly the case for Harge Volume parenterals.

Plastic containers may be principally composed of thermoplastic polymers. Plastic materials may additionally comprise additives, for example plasticisers, fillers, antioxidants, antistatic agents and other ingredients known in the art for specific purposes. Plastics suitable for use in the present invention are preferably resistant to the elevated temperatures required for thermal sterilisation. Preferred plastic containers are plastic infusion bags made from non-PVC plastics materials and are known in the art.

A primary concern of container systems is the protection they afford a solution against UV degradation. If desired, amber glass employing iron oxide or an opaque cover fitted over the container may afford the appropriate UV protection.

A wide range of container sizes may be employed. Container size may be conveniently categorised as Low-Volume, i.e. 100 ml or less and High-Volume, i.e. above 100 ml and typically 250 ml. In view of the relatively low solubility of the active agents in water, for example COMPOUND A which has a solubility of 3.2 to 4.2 mg/ml at 25° C. and pH of 5.8 to 6.0, it is preferable to use a High-Volume parenteral formulation, e.g. above 100, more particularly 250 ml in order to have an effective amount of active agent in a single container. Low-Volume parenteral formulations could of course be employed but this may require the use of an organic co-solvent or other solubilising aid which is less desirable than a totally water-based formulation.

Accordingly, in another embodiment of the invention there is provided a single dosage form of an active agent, e.g. COMPOUND A in an entirely water-based solution in a container which dosage form contains an effective amount of said active agent. In a more preferred embodiment, the single dosage form contains 600 mg COMPOUND A in 240 ml water. Preferably, when the single dosage form contains 600 mg of COMPOUND A in 240 ml water, the isotonic agent is glucose, preferably in an amount of 4.75% by weight.

Notwithstanding that it may be preferable to employ organic co-solvents in Low-Volume parenteral formulations, the Low-Volume parenteral formulation offers the advantage of being easier to store and use. Furthermore, the containers used for Low-Volume parenteral formulations have a smaller head space when filled which contains less oxygen (air) than the larger containers needed for High-Volume parenteral formulations. Containers used in Low-Volume parenteral formulations therefore are more easily purged of air, e.g using nitrogen or other inert gases.

It is a feature of Low-Volume parenteral formulations that for an i.v. solution sealed in a container and purged of air using nitrogen, the active agent, e.g. COMPOUND A may not be subjected to oxidative degradation during prolonged periods of storage, e.g. up to 24 months. This may be the case, irrespective of the choice of isotonic agent, e.g. NaCl or glucose. Whereas for High-Volume parenteral formulations, oxidative degradation of the active agent, e.g. COMPOUND A may be observed even after a nitrogen purge if isotonic agents other than glucose, e.g. NaCl are employed. In High- and Low-Volume parenteral formulations employing glucose as an isotonic agent, the active agent, e.g. COMPOUND A may not be subject to oxidative degradation over prolonged periods of storage, e.g. up to 24 months irrespective of whether the filled container is or is not purged with nitrogen.

Containers for use in the storage of the parenteral formulations according to the invention may be used to administer a single dose of active agent. The device used to convey the parenteral formulation from the container into the body of a patient may be any of the devices commonly used in the art to deliver therapeutic agents as parenteral formulations from containers, such as High- or Low-Volume containers as aforementioned.

Although the contact time between the device and the parenteral formulation may usually be brief, it may nevertheless be intimate, and therefore compatability with the injectable formulation should be assured. Accordingly, the material of the device may be the same as the containers or may include other materials commonly used in such devices if short term contact therewith is acceptable.

Although, as stated hereinabove certain active agents, e.g. COMPOUND A when used in conjunction with glucose as the isotonic agent may not be susceptible to oxidative degradation, as a precaution the process of filling containers may be carried out under an inert atmosphere, e.g. nitrogen.

The process of filling containers with the parenteral formulation should be carried out under sterile, aseptic conditions according to procedures well known in the art. Preferably the process is carried out in a Grade C clean area (Class 10,000). The parenteral formulation prepared as hereinabove described may be filtered under nitrogen pressure through a sterile filter with, for example a 0.22 micron pore size and collected into the containers. Thereafter, the containers may be stoppered and sealed, provided with an opaque, e.g. aluminium foil cover and heated in an autoclave at a temperature above about 121° C. for about 15 minutes.

The parenteral formulations according to the invention and packaged in containers as described above are stable both to the sterilisation process at elevated temperature in a autoclave and to prolonged periods of storage.

Parenteral formulations containing an active agent, e.g. COMPOUND A and glucose may be stable during storage at a temperature 25° C. for at least 24 months, with or without nitrogen purging.

Low-Volume parenteral formulations containing an active agent, e.g. COMPOUND A and NaCl as the isotonic agent may be stable during sterilisation at elevated temperature and storage at a temperature of 2 to 8° C. for at least 10 months, whereas Low-Volume injectable formulations containing an active agent, e.g. COMPOUND A and glucose as the isotonic agent may be stable during sterilisation at elevated temperature and storage at a temperature of 25° C. for at least 24 months.

Parenteral formulations according to the invention exhibit anticonvulsive action and are useful for initiating anti-convulsant therapy in patients experiencing seizures, e.g. resulting from new onset epilepsy, status epilepticus, cerebrovascular disorders, head injury and alcohol withdrawal. They are also useful as a replacement therapy when the administration of established courses of oral anticonvulsants is not possible, e.g. in cases of patients who cannot swallow, are vomitting, are unconcious or who are undergoing surgery.

Doses of up to 10 mg/Kg may be administered intravenously. The exact dosage required and the duration of administration will depend upon the seriousness of the condition being treated and the rate of administration. The preferred active agent, COMPOUND A, may be administered in dosage form of 600 mg up to 4 times a day. A preferred single dose may be 600 mg/240 ml. Preferably a dose may be delivered at a rate of 240 ml over a 30 minute period. As the dose may be delivered intravenously, the dose received and the blood concentration can be determined accurately on the basis of known in vitro and in vivo techniques.

There now follows a series of examples to illustrate the invention.

EXAMPLE 1

COMPOUND A is dissolved under a nitrogen blanket with stirring at 60–80° C. in water for injection (WFI) at a concentration of 2.5 mg/ml. After cooling to room temperature anhydrous glucose for injection is added and dissolved by stirring under nitrogen purging to obtain a 4.75% concentration glucose in water. After filtration through 0.22 micrometer pore size filter, the solution is purged with nitrogen, filled in glass vials (class II quality), sealed with a rubber closure and alu-cap and sterilized by autoclaving at 121° C. for 15 minutes.

The vials are stable and clear of coloured particles for at least two years at 2–8° C.

EXAMPLE 2

COMPOUND A was dissolved with stirring at 60–80° C. in WFl at a concentration of 2.5 mg/ml. After cooling to room temperature glucose for injection (anhydrous) is added and dissolved by stirring to obtain a 4.75% concentration of glucose in water. After filtration through 0.22 micrometer pore size filter, the solution is filled in glass vials, sealed with a rubber closure and alu-cap and sterilized by autoclaving at 121° C. for 15 minutes.

The vials are stable and clear of coloured particles for at least three months at 2–8° C.

EXAMPLE 3

COMPOUND A was dissolved under a nitrogen blanket by stirring at 60–80° C. in WFI at a concentration of 2.5 mg/ml. After cooling to room temperature sodium chloride is added and dissolved with stirring under nitrogen purging to obtain a 0.9% concentration of sodium chloride in water. After filtration through 0.22 micrometer pore size filter, the solution is purged with nitrogen, filled in glass vials, sealed with a rubber closure and alu-cap and sterilized by autoclaving at 120° C. for 15 minutes.

The vials are inspected after three months storage at 2–8° C. and show the presence of red coloured particles.

EXAMPLE 4

COMPOUND A is dissolved with stirring at 60–80° C. in WFI at a concentration of 2.5 mg/ml. After cooling to room temperature sodium chloride is added and dissolved by stirring to obtain a 0.9% concentration of sodium chloride in water. After filtration through 0.22 micrometer pore size filter, the solution is filled in glass vials, sealed with a rubber closure and alu-cap and sterilized by autoclaving at 121° C. for 15 minutes. The solutions in the vials show within six weeks storage at 2–8° C. the presence of red coloured particles.

What is claimed is:

1. A parenteral formulation consisting essentially of 10-oxacarbazepine, water, and glucose.

2. The formulation according to claim 1 wherein the glucose is present in an amount of from 4.75 weight percent, based on the total weight of the parenteral formulation.

* * * * *